United States Patent [19]

Kassis et al.

[11] Patent Number: 4,994,557
[45] Date of Patent: Feb. 19, 1991

[54] RADIOHALOGENATED HALF-ANTIBODIES AND MALEIMIDE INTERMEDIATE THEREFOR

[75] Inventors: Amin I. Kassis, Chestnut Hill; Leslie A. Khawli, Newton Centre, both of Mass.

[73] Assignee: President and Fellows of Harvard College, Cambridge, Mass.

[21] Appl. No.: 150,132

[22] Filed: Jan. 29, 1988

[51] Int. Cl.$^5$ .................... C07D 207/27; A61K 37/00
[52] U.S. Cl. ..................................... 530/391; 548/549
[58] Field of Search ........................ 548/549; 530/391

[56] References Cited

U.S. PATENT DOCUMENTS 4,111,937 9/1978 Ackerman ...................... 548/549 X
4,207,308 6/1980 Spenney .............................. 530/391
4,735,792 4/1988 Srivestava ...................... 548/549 X

OTHER PUBLICATIONS

Design and Synthesis of a New N-[p-$^{125}$I]-Iodophenyl-)-Maleimide ([$^{125}$I]IPM) "KIT" for Labeling of Antibodies with $^{131}$I and $^{123}$I-P. C. Srivastava et al., J. Nuclear Medicine, vol. 28, 726 (No. 717) (1987).
European Patent Application Publication EP No. 0203764 A2-Wilbur et al., Radiohalogenated Small Molecules for Protein Labeling, (Published Dec. 3, 1986).
Method for Radiohalogenation of Proteins Resulting in Decreased Thyroid Uptake of Radioiodine, Zalutsky et al., Appl. Radiat. Isotopes, vol. 38, No. 12, 1051–1055 (1987).
An Improved Method for the Radiohalogenation of Monoclonal Antibodies, Zalutsky et al., from: Immunological Approaches to the Diagnosis and Therapy of Breast Cancer, Edited by Roberto L. Ceriani (Plenum Publishing Corp., 1987).
N-(p-Iodophenyl) Maleimide, A New Radioiodinated Thiol Reagent With Selective Effects on Platelet Membrane Functions-P. C. Srivastava et al., J. Nuclear Medicine, vol. 27, 1046 (No. 697) (1986).
Synthesis and Radioiodination of Iodophenyl Conjugates for Protein Labeling M. Hylarides et al., J. Nuclear Medicine, vol. 28, 560 (No. 14) (1987).
Evaluation of Radioiodinations and Conjugations of 4-Iodobenzoates for Protein labeling-S. W. Hadley et al., J. Nuclear Medicine, vol. 28, 725 (No. 712) (1987).
Method for Radiohalogenation of Proteins Resulting in Increased Retention of Label In Vivo-A. S. Narula et al., J. Nuclear Medicine, vol. 28, 725 (No. 715) (1987).
Radioiodination of Monoclonal Antibodies Labeling with Para-Iodophenyl (PIP) Derivatives for In Vivo Stability of the Radioiodine Label-D. S. Wilbur et al., J. Nuclear Medicine, vol. 27, 959 (No. 335) (1986).
Synthesis and Radioiodinations of Some Aryltin Compounds for Radiolabeling of Monoclonal Antibodies, D. S. Wilbur et al.,-Poster from Sixth International Symposium on Radiopharmaceutical Chemistry, Boston, Jun. 1986.
Evaluation of Radioiodinated Monoclonal Antibody Conjugates which are Resistant to In Vivo Deiodination-S. Wilbur et al.-Poster and Abstract from Second International Conf. on Monoclonal Antibody Immunoconjugates for Cancer, Mar. 1987.
Layne et al., J. of Immunological Methods, vol. 96, pp. 195–199 (1987).
Wursthorn et al., J. Organometallic Chem., vol. 140 pp. 29–39 (1977).
Brennan et al., Science, vol. 229, 81–83 (1985).

Primary Examiner—David B. Springer
Attorney, Agent, or Firm—Fish & Richardson

[57] ABSTRACT

N-(m-radiohalophenyl) maleimide can be conjugated with a reduced antibody having a mercapto group to provide a radiolabelled half-antibody having immunological specific binding characteristics of whole antibody.

2 Claims, No Drawings

RADIOHALOGENATED HALF-ANTIBODIES AND MALEIMIDE INTERMEDIATE THEREFOR

This invention was made with Government support and the U.S. Government has certain rights in the invention under Contract No. DE-FGO2-86-ER-60460 with the Department of Energy.

This invention relates to radiohalogenated labelling of antibodies, preferably monoclonal antibodies, for use as physiological imaging agents or as therapeutic agents, and to an intermediate compound useful for making such agents. It has previously been proposed to label antibodies with various radiolabels. However, the harsh conditions required for introducing radiolabels directly into the antibody molecule tend to affect deleteriously the specific binding sites of the antibody, diminishing its specific binding capacity. It has also been proposed to dissociate antibodies by reduction of one or more disulfide bonds, resulting in half antibodies each of which retains one heavy and one light chain of the antibody and also retains the immunological specific binding capacity of the original antibody, and which contains at least one mercapto or thiol group covalently bonded to it, as taught in Layne et al., J. of Immunological Methods, Vol. 96 195-199 (1987); Brennan et al., Science, Vol. 229, 81-83 (1985).

It has now been found that N-(m-radiohalophenyl) maleimide can be covalently bonded to a half antibody through its free mercapto group to form a radiolabelled half antibody without destroying the immunological specific activity of the half antibody. The labelled half antibody thus produced will exhibit high resistance to cleavage in vivo together with immunological specificity approximating that of the original antibody. The product can be represented as having the following structure:

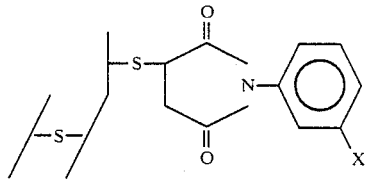

where X is a radiohalogen atom.

The maleimide can be made by first reacting a m-haloaniline with a hexaalkyl tin compound in the presence of a catalyst such as tetrakis (triphenyl phosphine) palladium to form m-aminophenyltrialkylstannane. The alkyl groups present may contain from 1 to 10 carbon atoms m-Aminophenyltrialkyl- stannane is preferred over the corresponding p-aminophenyltrialkylstannane (Wursthorn et al., J. Organometallic Chem., Vol. 140, 29-39 (1977)) because of the high stability of the former The stannane can then be reacted with maleic anhydride to form the corresponding maleamic acid which is readily dehydrated by of means of acidic anhydride to form N-(m-trialkylstannylphenyl) maleimide.

The trialkylstannyl group can by replaced by the desired radiohalogen atom, either before or after formation of the maleamic acid or maleimide, by reaction with an alkali metal radiohalide by means of the conventional Chloramine T procedure. Any radioactive halogen isotope can be used such as those of chlorine or bromine, but radioactive iodine or astatine is preferred.

Any desired antibody can be used, preferably a monoclonal antibody such as one which binds specifically to a tumor in vivo. The desired antibody can be split into half antibodies by reduction with dithioerythritol or with 2-mercaptoethyl amine.

The high stability of the m-trialkylstannyl aniline (also known as m-aminophenyltrialkylstannane) results in little decomposition during conversion to the maleimide and the subsequent substitution of the radiohalogen atom for the trialkyl stannyl group. The stability is carried over into the labelled half antibody which will exhibit little cleavage in vivo.

The following specific examples are intended to illustrate more clearly the nature of the present invention without acting as a limitation upon its scope.

EXAMPLES m-Aminophenyltributylstannane

A mixture of m-bromoaniline (1.26 g, 7.3 mmol), hexabutylditin (5.20 g, 8.9 mmol) and tetrakis(triphenylphosphine)palladium (79.0 mg, 0.07 mmol) in toluene (10 mL) was stirred and heated to 105° C. for 12 hours under nitrogen atmosphere. As the reaction proceeded, the mixture turned to black. The resulting black mixture was filtered, and the filtrate obtained was evaporated to dryness under reduced pressure at 50° C. The residue obtained was dissolved in hexane and the solution was applied to a flash chromatography column (30 mm×200 mm) of Kieselgel 60, 230 400 mesh. Elution was initiated with hexane (100 mL, giving fractions 1-10) followed by 2% ethyl acetate in hexane (100 mL, giving fractions 11-20) and 4% ethyl acetate in hexane (200 mL, giving fractions 21-40). All fractions were analyzed by thin layer chromatography on silica gel on GHLF plates, visualized by UV and (in the case of tin products) also by 5% phosphomolybdic acid in ethanol; where $R_f$ values are for EtOAc/hexane (4:100). Fractions 3-10 contained hexabutylditin; $R_f$ 0.8, while fractions 32-40 contained starting material 1; $R_f$ 0.25. Fractions 18-30, which showed a single spot at $R_f$ 0.4, were combined and the solvent were evaporated off to provide pure m-aminophenyltributylstannane 2 (2.3 g, 82%): $^1$H NMR (CDCl$^3$, δ); 7.2 (triplet, 1H, J=7 Hz, aryl C5-$\underline{H}$); 6.9 (doublet, 1H, J=7 Hz, aryl C4-$\underline{H}$); 6.8 (singlet, 1H, aryl C2-$\underline{H}$); 6.6 (doublet, 1H, J=7 Hz, aryl C6-$\underline{H}$); 3.6 (singlet, 2H, N$\underline{H_2}$); 0.9-1.7 (multiplets, 27 H, 3 X $\underline{n-C_4H_9}$).

Analysis calculated for $C_{18}H_{33}NSn$: C, 56.57; H, 8.70; N, 3.66. Found: C, 56.56; H, 8.72; N, 3.72.

N-(m tri-n butylstannylphenyl)maleamic acid

Maleic anhydride (0.18 g, 1.8 mmol) was dissolved in toluene (2 mL). m-Aminophenyltributylstannane as described above (0.70 g, 1.8 mmol) in toluene (4 mL) was added dropwise over a 5 minute period. After the addition was complete, the reaction mixture was stirred for 15 minutes at room temperature then cooled in an ice-water bath. The precipitaed yellow product N-(m-tri-n-butylstannylphenyl)maleamic acid was collected by vacuum filtration, recrystallized from toluene and dried overnight in a vacuum dessicator (0.75 g, 85%): mp. 130°-131° C. $^1$H NMR (Me$^2$SO-d$^n$, δ); 10.4 (singlet, 1H, O$\underline{H}$); 7.6 (singlet, 2H, aryl C2-$\underline{H}$ and aryl C6-$\underline{H}$); 7.3 (triplet, 1H, aryl C5-$\underline{H}$); 7.2 (doublet, 1H, aryl $\overline{C4}$-$\underline{H}$); 6.4 (doublet of doublets, 2H AB, J=12 Hz, 2 CHC=$\overline{O}$); 0.9-1.6 (muliplets, 27H, 3×n-$\underline{C_4H_9}$).

Analysis calculated for $C_{22}H_{33}NO_3Sn$: C, 55.02; H, 7.34; N, 2.91. Found: C, 54.90; H, 7.55; N, 2.88

N-(m-tri-n butylstannylphenyl)maleimide

N-(m tri-n butylstannylphenyl)maleamic acid prepared as described above (0.40 g, 0.83 mmol) was placed in acetic anhydride (6 mL). Sodium acetate (0.43 g) was added and the solution stirred for 15 minutes at room temperature. After the reaction became homogeneous, the reaction mixture was stirred for 3 hours at 120° C. The filtrate obtained from this brown mixture was evaporated to dryness under reduced pressure and the residue was dissolved in ethyl ether. The ether mixture was filtered and the filtrate was again evaporated to dryness The compound was obtained by flash chromatography on a 30×200 mm column of Kieselgel 60, 230-400 mesh, eluted with ethyl acetate/hexane (1:5) (100 mL) to yield ten fractions. Fractions 6-9 were combined to give the desired product as an orange oil (0.3, 78%): TLC (EtOAc/hexane, 1:5) $R_f$ 0.30; $^1H$ NMR (CDCl$_3$), δ); 7.3-7.5 (multiplets, 4H, 4 aryl C$\underline{H}$); 6.8 (singlet, 2H, 2 CHC=O); 0.9-1.6 (multiplets, 27H, 3×n-C$_4$H$_9$).

Analysis calculated for $C_{22}H_{33}NO_2Sn$: C, 57.17; H, 7.19; N, 3.03. Found: C, 57.02; H, 7.21; N, 2.97

N-(m-iodophenyl)maleimide

METHOD A.

To a stirred solution of sodium iodide (32 mg, 0.21 mmol) in H$_2$O (100 μL), was added N-(m-tri-n-butylstannylphenyl)maleimide as described above (0.1 g, 0.21 mmol) in CH$_2$Cl$_2$ (2 mL), followed by a solution of chloramine-T (59 mg, 0.21 mmol) in H$_2$O (2 mL). Reaction progress was followed by TLC on silica gel GHLFC plates (EtOAc/hexane, 1:3), starting material 4 $R_f$ 0.65. The reaction mixture was stirred at room temperature for 30 minutes. The mixture initially turned yellow from the formation of I+. The solution rapidly became lighter until a colorless solution resulted. To this was added 2 mL of 5% aqueous sodium bisulfite and the resulting mixture was extracted with dichloromethane (4×10 mL). The dichloromethane extracts were dried (MgSO$_4$), and the solvent was removed in vacuo to give the desired product N-(m-iodophenyl)-maleimide (60 mg/ 95%): TLC (EtOAc/hexane, 1:3) $R_f$ 0.42; mp 154°–155° C. $^1H$ NMR (CDCl$_3$, δ); 7.1-7.7 (multiplets, 4H, 4 aryl C$\underline{H}$); 6.8 (singlet, 2$\underline{H}$, 2 C$\underline{H}$C=O).

METHOD B

Maleic anhydride (0.89 g, 9.07 mmol) was dissolved in toluene (10 mL) and m-iodoaniline (2 g, 9.13 mmol) in toluene (15 mL) was added dropwise over a 20 minute period. After the addition was complete, the reaction mixture was stirred for 45 minutes at room temperature then cooled in an ice water bath. The precipitated yellow product, N-(m-iodophenyl)maleamic acid, was collected by vacuum filtration, washed with hexane and dried overnight (2.7 g, 94%): mp. 197°–198° C.; $^1H$ NMR (Me$_2$SO-d$_6$, δ); 10.3 (singlet, 1H, OH); 8.1 (singlet, 1H, aryl C2-$\underline{H}$); 7.5 (doublet, 1H, J=7 Hz, aryl C6 -$\underline{H}$); 7.3 (doublet, 1H, J=7 Hz, aryl C4-$\underline{H}$); 7.1 (triplet, 1H, aryl C5-$\underline{H}$); 6.4 (doublet of doublets, 2H, AB, J=12 Hz, 2 C$\underline{H}$ C=O).

N-(m-iodophenyl)maleamic acid (1 g, 3.15 mmol) was placed in acetic anhydride (10 mL). Sodium acetate (1 g) was added and the solution stirred at 120° C. The dark brown filtrate was evaporated to dryness under reduced pressure and the residue was dissolved in diethyl ether. The ether mixture was filtered and the filtrate was again evaporated to dryness. The residue obtained was applied to a flash chromatography column (30×200 mm) of Kieselgel 60, 230-400 mesh). Elution with ethyl acetate/hexane (1:3) (400 mL) yielded forty fractions. Fractions 25-35 were combined to provide pure pale yellow N-(m-iodophenyl)maleimide (0.75 g, 80%): TLC (EtOAc/hexane, 1:3) $R_f$ 0.42; mp 154°–155° C.; $^1H$ NMR (CDCl$_3$, δ); 7.1-7.7 (multiplets, 4H, 4 aryl CH); 6.8 (singlet, 2H, 2 CHC=O ).

Analysis calculated for $C_{10}H_6NO_2I$: C, 40.16; H, 2.01; N, 2.01; N, 4.68. Found: C, 40.51; H, 2.13; N, 4.61.

N-(m-[$^{125}$I]iodophenyl)maleimide

In a 5-mL test tube containing sodium [$^{125}$I] iodide (15 μCi) was added 100 νL of a 40 mM aqueous solution of Chloramine-T. To this was added 500 νL of 6 mM CH$_2$Cl$_2$ solution of N-(m-tri-n-butylstannyl phenyl)-maleimide. The reaction was stirred vigorously for 30 minutes at room temperature and extracted with 4 × 1.5 mL portions of CH$_2$Cl$_2$. The CH$_2$Cl$_2$ layers were removed with a Pasteur pipet, and washed once with 5% aqueous sodium bisulfite solution. The organic solvent was evaporated under a stream of N$_2$ and chromatographed on Kieselgel 60, 230-400 mesh using an 8 × 100 mm disposable column (BioRad) Elution was initiated with hexane (4 mL, giving fractions 1-4) followed by 35% ethyl acetate in hexane (12 mL, giving fractions 5-16). Fractions 8-12 showed one spot on TLC autoradiography and indicated that the radioactivity comigrated with radioinert (N-(m-iodophenyl) maleimide, by using ethyl acetate/hexane (1:1), $R_f$ 0.64. The desired fractions were combined and were measured using a radioisotope calibrator give 8.7 μCi ofc m-[$^{125}$I]PM (4, 73% radiochemical yield). Fractions 5 and 6 constituted 8% of the radioactivity containing products and were accounted for by a compound with $R_f$ 0.77. The identity of this side product was not determined.

Reduction of Rabbit IgG Model of Antibody

The subunits (half-IgG containing single heavy-light chains) were prepared by the method of Layne et al., supra. Typically, 8 mg of rabbit IgG was dissolved in 1 mL of Tris HCl (pH 8) and reduced with a solution of dithioerythritol (45 νg in 1 mL of Tris HCl, pH 8). The reaction mixture was left for about 40 minutes at room temperature and quenched by adding 100 μL of glacial acetic acid. The heavy light-half moleculed was isolated and purified by HPLC using size exclusion column, protein Pak 300 SW (Waters Assoc., Milford, Mass.); the mobile phase was 2.5% triethylamine in 0.1M citrate buffer at pH 6. The UV absorbances were detected at 280 nm. The HL content was estimated by using the Beer's Law plots for HL constructed from the HPLC peak heights.

Reaction of Rabbit IgG Subunits (HL) Model of Antibody and N-(m-[$^{125}$I]iodophenyl)maleimide: Preparation of Covalently Bound Conjugate N-(m [$^{125}$I]iodophenyl)maleimide obtained as described above in the eluant from the silica gel column was transferred to a glass vial, evaporated to dryness with a stream of nitrogen, and dissolved in 15 μl of methanol. Rabbit IgG subunits dissolved in 0.1M citrate buffer pH 6 (2.7 mg/mL was added immediately to m-[$^{125}$I]PM solution (1 equiv. RIgG subunits/1.5 equiv. m-[$^{125}$I]PM). The reaction was allowed to proceed for 30 minutes at 37° C. Sephadex G-50 (fine) was swollen overnight in the buffer used for elution. A column 1×14 cm (BioRad) was prepared and the radiolabeled antibody conjugate (HL-m-[$^{125}$I]PM) was isolated and purified on the Sephadex G-50 column as follows. The reaction mixture was put on the column slowly and allowed to stand 15 minutes before elution. The radioactive conjugate was then eluted with 0.01 M PBS buffer pH 7.2 at a flow rate of about 0.25 mL/min with collection of 0.5 mL aliquots. Individual tubes were collected and counted in a gamma counter. Tubes 3 and 4 contained the labeled conjugate. The desired conjugate was recovered in 70% yield.

Preparation of Immunoglobulin-SPDP(Ig-SPDP): Determination of 2-pyridyl disulfide groups per Ab molecule Rabbit IgG (10 mg) was dissolved in 2 mL of 0.1M sodium phosphate buffer containing 0.1M NaCl (pH 7.5) and treated with an ethanol solution of N-succinimidyl-3-(2-pyridyl-dithio)propionate (SPDP) (2-5 equiv. of 9.6 mM solution). The SPDP solution was added in aliquots over a period of 30 minutes. The unreacted SPDP and N-hydroxy-succinimide formed were removed by gel filtration on Sephadex G-25 column (1×14 cm) that was equilibrated with 0.1M sodium phosphate buffer/0.1M NaCl (pH 7.5) and the SPDP-coupled protein eluted with same buffer.

The average number of 2-pyridyl disulfide groups attached to each IgG molecule was determined by the method of Stuchbury et al., Biochem. J., Vol. 15, 417–432 (1975). The assay uses the change in absorbance at 280 nm which occurs when 2-pyridyl disulfide group couples to the antibody Briefly, the absorbance at 280 nm of a suitable aliquot of the modified IgG was determined. This aliquot was then mixed with 100 μL of 50 mM dihierythritol in water and the absorbance was determined immediately at 343 nm (molar absorptivity = $8.08 \times 10^3$). From this treatment, the amount of pyridine 2-thione released was determined and the content of SPDP in the modified IgG was calculated by using the following expression: concentration of pyridine-2-thione released on reduction $\times 5100 = A_{280}$ due to 2-pyridyl sulfide group.

Reaction of Ig-SPDP with Dithioerythritol: Preparation of Ig-SH

The immunoglobulin-2-pyridyl disulfide derivative (Ig-SPDP) was then transferred o 0.1M sodium acetate buffer containing 0.1M NaCl (pH 4.5). This was achieved by centrifugation three times using a Centricon microconcentrator (Amicon Co.). Following each centrifugation, the sample was diluted in the sodium acetate buffer, pH 4.5 and the final volume was kept the same. The final solution of Ab SPDP was added to 100 μL ofc 25 mM dithioerythritol dissolved in the same buffer. The reaction was allowed to progress for 30 minutes at room temperature. At this point, the thiolated antibody was separated by gel filtration using sephadex G-25 column (1×14 cm) with PBS 0.1M, pH 7.5. Reaction of Ig-SH and N-(m-[$^{125}$I]iodophenyl)-maleimide The conjugation was accomplished by addition of 1 equiv. of thiolated IgG (0.1M PBS, pH 7.5) to N-(m [$^{125}$I]iodophenyl)maleimide dissolved in methanol Complete separation of the labeled conjugate was achieved as described for the conjugate of Rabbit IgG described above. It was recovered in 40% yield.

Attempts to radiolabel bovine serum albumin using identical conditions afforded about 80% conjugation yield.

Determination of Radiochemical Purity

All conjugated proteins were analyzed using an instant thin layer chomatography (ITLC) system consisting of silica gel impregnated glass fiber (Gelman Sciences, No. 61886). Strips (2×20 cm) were spotted with 1 μL of sample, air dried and immediately separated in MeOH/H$_2$O (80:20) for approximately 12 cm, again air dried, cut in halves and counted to determine protein bound and non protein bound radioactivity. The radioiodine labeled proteins gave an $R_f$ value of 0 and showed a radiochemical purity of 100%.

Serum Stability of Radioiodine Labeled Proteins

The serum stability of proteins labeled with N-(m [$^{125}$I]iodophenyl)maleimide was determined in vitro as follows a solution of radiolabeled protein conjugate (1 mg/mL) in 0.01M PBS at pH 7.2 was added to fresh mouse serum at 37° C. to a stop concentration or 100 μg/mL. At 1 minute, 1 h, 3 h, 6 h, and 24 h protein bound activity was determined by adding 900 μL of 10% trichloroacetic acid (TCA) to 100 μL of each aliquot. After incubation at room temperature for 5 minutes, protein precipitates were sedimented by centrifugation; 500 μL samples of supernatant were withdrawn from each tube and counted for radioactivity in a gamma counter. The counts of the tube containing the precipitates were also measured. The percentage of counts precipitated was calculated as $$\frac{(\text{cpm of precipitates} + 500\ \mu\text{L supernatant}) - (\text{cpm of 500}\ \mu\text{L supernatant})}{(\text{cpm of precipitates} + 500\ \mu\text{L supernatant}) - (\text{cpm of 500}\ \mu\text{L supernatant})}$$

The radioactivity observed for radioiodine-labeled proteins demonstrate that they are stable to serum proteins in that the 1 minute and 24 hour percentage counts precipitated by TCA are almost identical (>99%) showing the activity present as protein bound. The non protein bound radioactivity in the supernatant (<1%) is probably free $^{125}$I label produced following dissociation of conjugate in serum.

Similar results can be obtained using other isotopes of iodine or astatine 211, and using various monoclonal antibodies in place of rabbit IgG.

What is claimed is:

1. N-(m-radiohalophenyl)maleimide.
2. Conjugate of N-(m-radiohalophenyl)maleimide with reduced antibody.

* * * * *